United States Patent [19]
Cravy et al.

[11] 4,165,744
[45] Aug. 28, 1979

[54] DYNAMIC KERATOMETRY AND KERATOSCOPY METHOD AND APPARATUS

[76] Inventors: Thomas V. Cravy, 2265 Fallen Leaf Dr.; Dennis D. Shepard, 333 Las Flores Dr., both of Santa Maria, Calif. 93454

[21] Appl. No.: 812,991

[22] Filed: Jul. 5, 1977

[51] Int. Cl.² ............................................. A61B 3/10
[52] U.S. Cl. .............................. 128/303.1; 128/745; 128/22; 351/6; 351/16; 351/13
[58] Field of Search ................... 128/303 R, 303.1, 21, 128/22, 23, 2 S, 2 T; 351/6, 16, 13

[56] References Cited
U.S. PATENT DOCUMENTS

| 3,248,162 | 4/1966 | Knoll | 351/13 X |
| 3,598,478 | 8/1971 | Townsley | 351/16 X |
| 3,645,609 | 2/1972 | Holmes | 351/13 X |

OTHER PUBLICATIONS

Hofstetter, "A Keratoscopic Survey of 13,395 Eyes", American Journal of Optometry and Archives, vol. 36, 1959 pp. 3 & 4.

Primary Examiner—Henry J. Recla
Attorney, Agent, or Firm—Fulwider, Patton, Rieber, Lee & Utecht

[57] ABSTRACT

A method and apparatus for performing dynamic keratometry and keratoscopy. The apparatus projects a substantially circumferentially continuous circle of light onto a cornea and the reflection from the cornea is observable in an unrefracted state through a central opening in the apparatus. Systematically varying the distance of the apparatus from the cornea does not significantly affect the sharpness of the unrefracted reflected image, affecting only its diameter so that the circle of light can be caused to pass over the entire cornea for dynamic examination of its curvature. A particular application of the apparatus is in evaluating the effects of surgery upon corneal curvature both during and after surgery. The method of the invention involves movement of a circle of light across all regions of the cornea from the center to the corneal periphery to determine curvature of the entire cornea.

15 Claims, 14 Drawing Figures

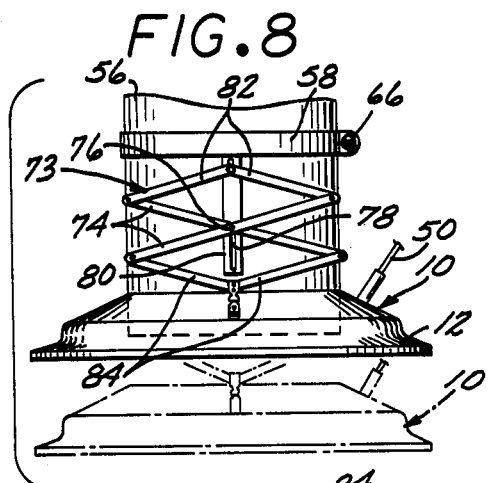
FIG.8
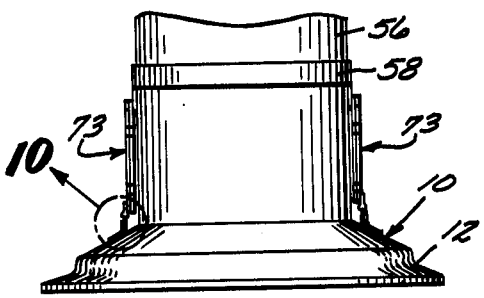
FIG.9
FIG.10
FIG.11
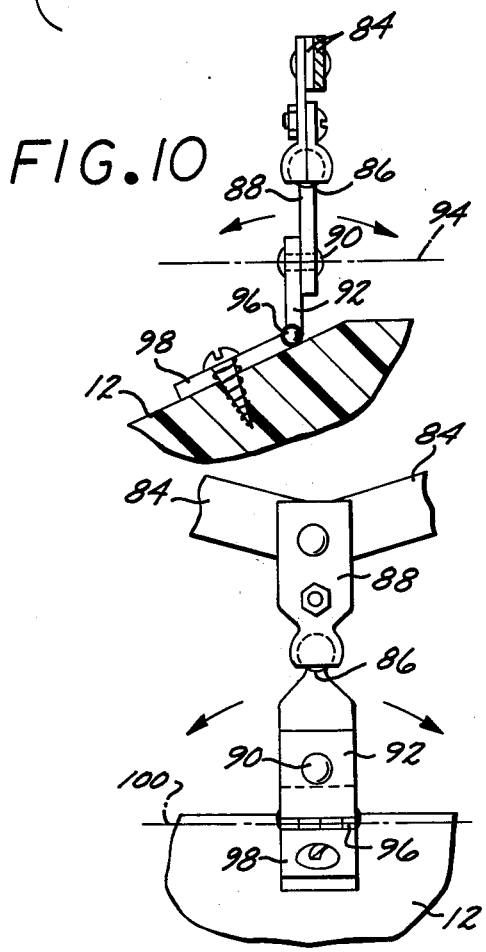
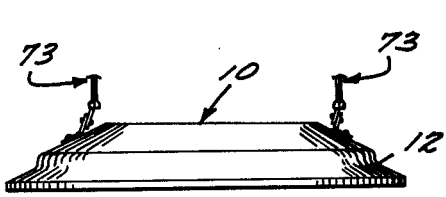
FIG.12
FIG.13
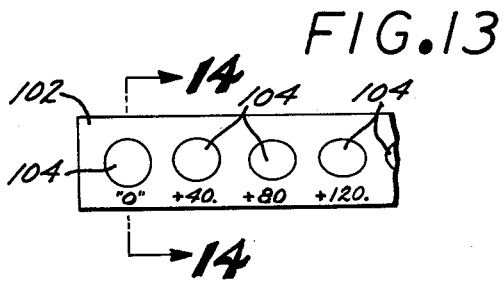
FIG.14
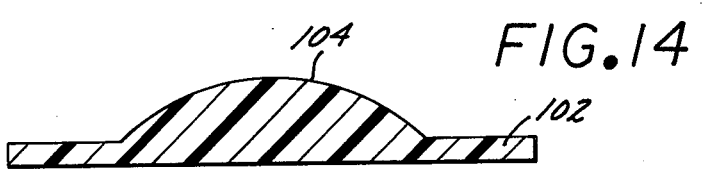

DYNAMIC KERATOMETRY AND KERATOSCOPY METHOD AND APPARATUS

BACKGROUND OF THE INVENTION

1. Field of the Invention

The present invention relates to a method and apparatus for practicing dynamic keratometry and keratoscopy.

2. Description of the Prior Art

Until relatively recently there was no satisfactory means for determining corneal curvature during eye surgery. In the absence of such a means a surgeon could not accurately establish the effects of the eye surgery upon corneal curvature at the actual time of surgery.

In some patients post-operative astigmatism was so great that it was difficult or impossible to satisfactorily correct the astigmatism through the use of glasses or contact lenses.

Richard D. Troutman, M.D., recently advanced a micro-surgical keratometer for evaluating the effects of eye surgery on corneal curvature. The keratometer is rigidly mounted directly to a surgical microscope of the type typically used for eye surgery. A fiberoptic bundle coupled to a light source is utilized to project upon the cornea a circle of discontinuous dots of relatively low light intensity visible to the surgeon when the operating room lights are shut off or dimmed. The microscope controls are operated to focus the circular dot image on the cornea, and the dot image is compared with measurements previously obtained through the use of a clinical quantitative keratometer. The microscope and keratometer are fixed in position to maintain proper image focus while observing, quantitatively, any change in the light dot pattern as the operation proceeds. The degree of distortion of the dot pattern relative to a perfect circle is established by comparing the relationship between the dot pattern and the microscope eyepiece reticles. A flat cornea reflects a dot pattern closer to the outer reticle of the eyepiece, while a steep cornea reflects a dot pattern closer to the inner reticle. The maintenance of the keratometer at a fixed distance from the cornea thus provides a measure of the degree of corneal curvature. Adjusting the cross hairs of the reticle to coincide with the long axis of a reflected oval dot pattern provides reference points for establishing the approximate amount of astigmatism or meridional error present. Since image focus and measurement of the degree of corneal curvature require that the keratometer be fixed, the system is incapable of providing dynamic keratometry. That is, it is not possible to dynamically detect meridional error of all positions of the meridia lying between the corneal center and corneal periphery. The focused dot pattern crosses each corneal meridian at only one point. In this regard, it is noted that the well known clinical Klein keratoscope projects concentric circles which cross each corneal meridia at more than one point. However, there is no means by which such an instrument can be utilized as an integral part of a surgical procedure to establish corneal curvature while the surgery is in progress, nor is the keratoscope adapted for establishing the corneal curvature of those portions of meridia located between the reflected concentric circular images. The keratoscope requires a fixed distance from the eye for focusing.

BRIEF SUMMARY OF THE INVENTION

The present invention relates to a method and apparatus for performing dynamic keratometry and keratoscopy. The method includes the step of projecting a substantially continuous circle of light onto a cornea from the apparatus housing onto a cornea or a test object for viewing the reflected image along an axis extending through the housing. The method further includes the step of moving the housing toward the cornea so that the image is reflected from the more peripheral portion of the cornea, and the step of moving the housing progressively away from the cornea whereby the diameter of the reflected image progressively diminishes toward the corneal center thereby to detect meridional errors throughout the angular length of the meridians extending between the corneal center and periphery. The method can also include the step of comparing the images reflected from the cornea and test objects to establish the degree of corneal astigmatism.

In use of the apparatus as a keratometer for performing dynamic surgical keratometry the apparatus comprises a housing having a central opening and a light projection means for projecting a substantially circumferentially continuous circle of light onto a cornea. The reflection from the cornea is observable through the central opening of the housing. The substantially continuous character of the circle enables ready detection of an astigmatic condition. The light source preferably utilized is a fluorescent lamp capable of projecting a relatively high level of light intensity at a relatively low heat level to enable use of the keratometer in a fully illuminated surgery operating room without significantly affecting the surgeon's ability to see the reflected light image.

The keratometer housing is supported for universal movement to permit systematic variance of the distance between the housing and the cornea, and also to permit lateral movement and angulation of the housing for orienting the housing perpendicular to the cornea regardless of the position of the eye. Such support for the housing can take the form of an adjustable parallelogram type of arm fixed at one end to a wall, for example, and mounting the keratometer housing at the other end. If the housing is to be attached to a surgical microscope or the like, the support can take the form of a scissors arm arrangement by means of which the housing can be carried by the microscope and yet be extensible and retractable relative to the microscope. Such arrangements enable the keratometer to be moved closer to the cornea to produce an image of relatively large diameter reflected from the corneal periphery, thereby enabling the surgeon to detect meridional errors in that area. The keratometer housing can also be gradually moved farther from the cornea to produce a progressively smaller image reflected from the corneal central area. This allows the surgeon to move the housing to progressively scan all areas between the corneal periphery and center for the detection of meridional errors.

A test bar mounting a series of test objects provides a means for training eye surgeons in the use of the present apparatus, and for establishing the degree of corneal astigmatism present in a cornea being examined. The test objects are provided with curvatures corresponding to increasing degrees of astigmatism. A comparison of the images reflected from such objects and the cornea affords a means for ascertaining the amount of corneal astigmatism which is present.

The apparatus can be hand held, if desired, and it can be used as a keratoscope. Consequently, in the description which follows, as well as in the claims, the terms "keratometer" and "keratometry" for brevity are intended to comprehend use of the present apparatus as a keratoscope in performing keratoscopy.

Other objects and features of the invention will become apparent from consideration of the following description taken in connection with the accompanying drawings.

BRIEF DESCRIPTION OF THE DRAWINGS

FIG. 8 is a front elevational, partially diagrammatic view illustrating the present keratometer mounted to the optical lens of a surgical microscope, the phantom lines indicating the keratometer moved closer to the cornea;

FIG. 9 is a side elevational view of the optical lens and keratometer of FIG. 8;

FIG. 10 is an enlarged view of the encircled section designated 10 in FIG. 9;

FIG. 11 is an end elevational view of the keratometer and a portion of the mounting means, illustrating the angulation capability of the mounting arrangement;

FIG. 12 is a side elevational view of the subject matter illustrated in FIG. 10;

FIG. 13 is a partial top plan view of a test bar; and

FIG. 14 is an enlarged view taken along the line 14—14 of FIG. 13.

DESCRIPTION OF THE PREFERRED EMBODIMENT

Figure 1:
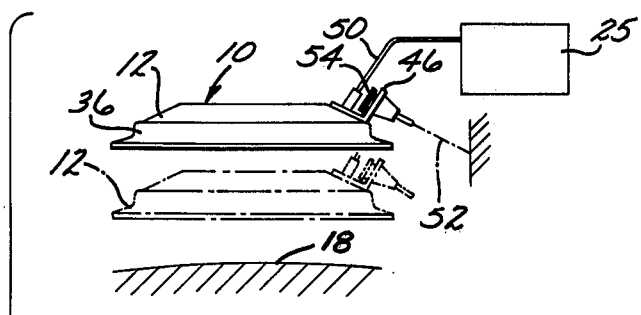
FIG. 1 is a front elevational, partially diagrammatic view illustrating the present keratometer, including a phantom line showing of the keratometer moved closer to the cornea.
Figure 2:
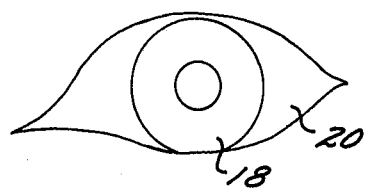
FIG. 2 is a simplified showing of the human eye, illustrating the approximate size and location of the cornea.

Referring now to the drawings, and particularly to FIGS. 1-4, there is illustrated a keratometer 10 according to the present invention and comprising, generally, a circular housing 12 having a central opening 14 and a light source in the form of a circular fluorescent tube 16 for projecting a substantially circumferentially continuous circle of light onto the cornea 18 of an eye 20. The light image 22 reflected from the cornea 18 is observable through the opening 14 along a central axis 24. The keratometer 10 also includes any of various support means operable to systematically vary the distance between the housing 12 and the cornea 18, as best illustrated in FIG. 1.

One form of light tube 16 which has operated satisfactorily is a fluorescent or neon-mercury type approximately 8 millimeters in diameter and arranged in a circular form approximately 5 inches in diameter. The tube 16 operates at 750 volts and 40 milliamps, and is supplied by a power source generally indicated at 25 and comprising a transformer (not shown) using 115 volt alternating current.

Figure 3:
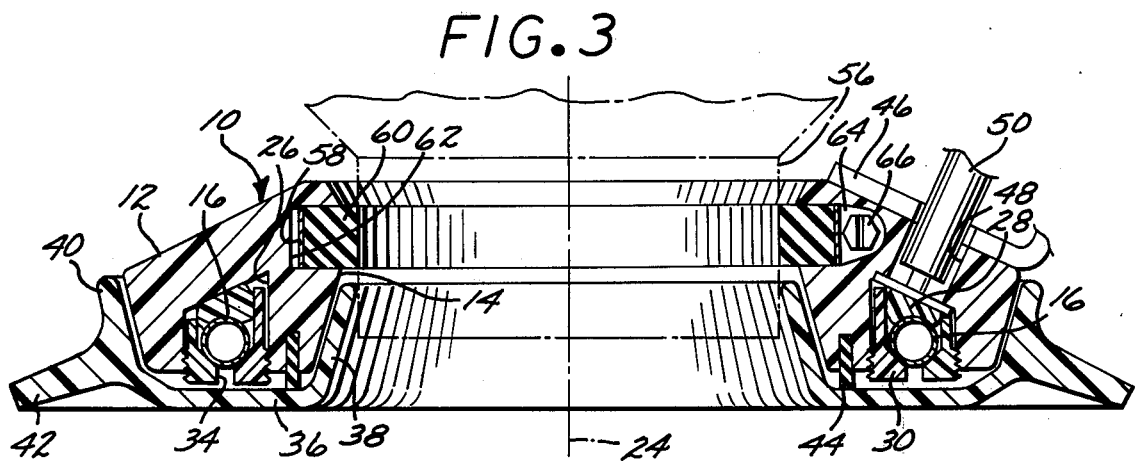
FIG. 3 is an enlarged transverse cross-sectional view of the keratometer of FIG. 1, including a phantom line showing of an optical instrument to which the keratometer can be mounted.
Figure 4:
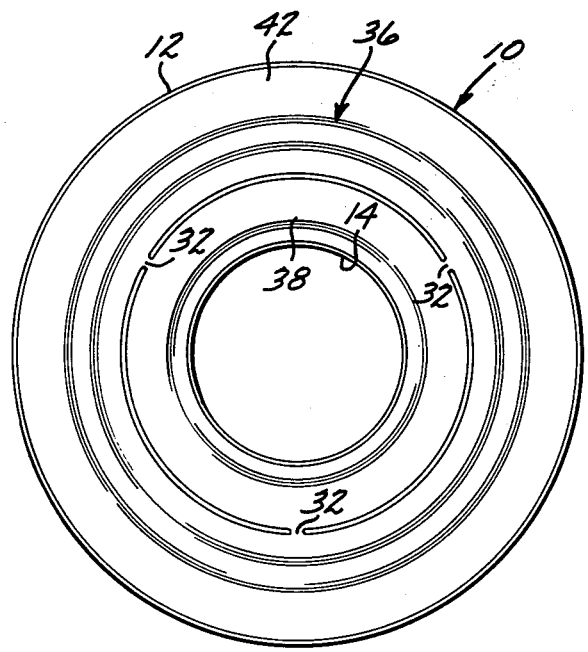
FIG. 4 is a bottom plan view of the keratometer.

As best seen in FIG. 3, the housing 12 includes an annular downwardly opening channel 26 within which the tube 16 is received. Tube 16 bears against a resilient material such as a urethane foam ring 28 which is seated against the base of the channel 26. The foam ring 28 cushions the tube 16 against breakage. In addition, the underside of ring 28 is preferably made reflective, as by applying a coating or layer of reflective material, to enhance light concentration upon the subject.

An annular ring or optical mask 30 is threadably mounted within the lower portion of the channel 26 and bears against the underside of the tube 16 to secure it in position. The mask may comprise separate coaxial annular portions threaded to the opposite, confronting walls of the channel 26, as illustrated, and spaced apart to define a substantially continuous circumferential aperture 34 about 1/16 inch in width. However, preferably such annular portions are connected together by three equally circumferentially spaced bridging portions 32 which divide the apertures 34 into three arcuate, individually circumferentially continuous openings located upon a common circumference. Another mask 30, not shown) having a greater width of aperture 34 can be utilized to provide more light where, for example, it is desired to take motion pictures or work without using any additional lighting. The margins defining the aperture 34 are machined or otherwise precisely formed so that as nearly perfect a circle of light as practicable is projected onto the cornea 18. The spaces or portions 32 between the three arcuate openings structurally tie together the adjacent portions of the mask 30. They are sufficiently narrow that they do not significantly affect detection by the surgeon of a noncircular reflection or image 22. The portions 32 can easily be eliminated, and thereby provide a circumferentially continuous circle of light as previously indicated, but the discontinuities in the circle of light caused by the presence of the portions 32 serve as reference points to orient the viewer. In certain apparatus of the prior art, as previously mentioned, a circle of spaced dots is projected and the spacings prevent detection of certain meridional errors which are readily apparent with the substantially continuous image 22 of the keratometer 10.

A transparent shield 36 underlies the housing 12 and includes an inner cylindrical portion 38 extending upwardly into the housing opening 14 and an outer cylindrical portion 40 surrounding and overlying the outer periphery of the housing 12. The portion 40 includes an annular grooved sterilizable and removable handle section 42 which can be used to move and position the keratometer 10.

A resilient spacer ring 44 fitted within an annular, downwardly opening groove provided in the underside of the housing 12 bears against the shield 36. The ring 44 maintains the shield 36 in spaced relation to the underside of the optical mask 30. The shield 36 is secured to the housing 12 by any suitable means. Such means may take the form of bayonet joints (not shown) which permit the shield 36 to be fitted to the housing 12, given a slight turn, and thereby be seated and retained in position, as is well known to those skilled in the art. Removable retaining screws or the like (not shown) may be used to prevent inadvertent rotation and separation of the shield 36 and housing 12. In any event, the particular interconnection utilized to secure together the shield 36 and housing 12 is not critical to the present invention, although it is desirable that the shield 36 be easily separable for sterilization.

An angle bracket 46 is attached in any suitable manner to the upper side of the housing 12 and includes an aperture aligned with an opening 48 provided in the housing 12. The opening 48 extends into the channel 26 which carries the fluorescent tube 16. An electrical cord 50 coupled to the power source 25 extends into the opening 48 and the electrical leads of the cord are suitably connected to the tube 16. The cord 50 is long enough to permit the keratometer 10 to be freely moved during use.

The bracket 46 also provides a means for connecting the keratometer 10 to a support means such as an arm 52, only a portion of which is shown in FIG. 1. The particular type of support means utilized to support the keratometer 10 is not critical to the present invention so long as the keratometer can be easily moved about and particularly toward and away from the cornea 18 during a surgical procedure. Thus, the support arm 52 can be an adjustable parallelogram type fixed at one end to a bench, or a wall, or a floor stand. Various other support means will suggest themselves to those skilled in the art and all such support means are intended to be included within the scope of the present invention.

The support arm 52 is preferably quickly detachable from the bracket 46, such as by manipulation of a thumb screw or the like so that, if desired, the keratometer 10 can be mounted to a microscope, camera or other optical instrument. The cylindrical barrel of the objective lens of an operating microscope is illustrated at 56 by way of example. Attachment of the keratometer 10 to the lens barrel 56 is conveniently provided by employing a clamping ring 58 fitted about a compression ring 60. The rings 58 and 60 are both located within an annular channel 62 which opens into the central opening 14 of the housing 12. The ring 58 includes usual end tabs 64 which are urgeable together by rotating a slotted screw 66 which is reached by providing a suitable opening (not shown) in the housing 12. The clamping action of the rings 58 securely holds the keratometer 10 in position upon the lens barrel 56.

In operation, the keratometer 10 utilizes the optical property of the cornea 18 to behave as a convex mirror. Assuming the keratometer is mounted to the support arm 52, the arm 52 and its capability for three dimensional mobility allow the keratometer 10 to be arranged squarely in front of the cornea 18. The fluorescent tube 16 is turned on and a substantially perfect circle of light is projected onto the cornea 18. The distance of the keratometer 10 from the cornea 18 determines the size of the reflected image 22 and the portion of the cornea from which the image is reflected. The closer the keratometer 10 is to the cornea 18, the larger the reflected image 22 and the more peripheral the cornea from which the image 22 is reflected. The farther the keratometer is from the cornea 18, the more central the portion of the cornea 18 utilized and the smaller the image.

Dynamic keratometry according to the present apparatus and method is performed by systematically varying the distance of the keratometer 10 from the cornea 18. The image 22 and the corneal surface itself are viewable through the central opening 18 by the naked eye, through surgical loupes or an operating microscope, or by independent camera means. Using the keratometer 10, the surgeon is able to perform surgery and simultaneously observe the effects of the surgery upon corneal curvature. If the technique of the surgeon involves the use of an operating microscope, the keratometer is easily detached from the support arm 52 and attached to the microscope lens barrel 56, as previously described. In this regard, it will be apparent that various reticles (not shown) may be placed across the central opening 14 or other viewing aperture to effect quantative keratometry, if desired.

Another attachment means for securing the keratometer 10 to the microscope objective lens or lens barrel 56 is illustrated in FIGS. 8–12.

Once the objective lens 56 is focused, the amount of permissible excusion before this focus is lost is relatively limited. The mounting means 72 enables the keratometer 10 to be moved appreciably toward and away from the cornea 18 independently of the lens 56. Various means can be provided to accomplish this, and the means 72 is therefore merely exemplary.

The mounting means 72 includes a pair of extensible and retractable devices or scissors mechanism 73 for location on opposite sides of the lens 56. Each mechanism 73 includes a pair of elongated links 74 which intersect and are pivotally connected at their mid-points by a pin connection 76. The pin connection 76 is longitudinally slidable within a slot 78 provided in an elongated bar or travel limiter 80, the upper end of which is fixedly attached to a band 58. The band 58, as in the embodiment illustrated in FIG. 1, is tightened in position about the lens 56 by means of a nut and bolt assembly 66.

Each scissors mechanism 73 also includes a pair of shorter upper links 82 pivoted at their inner ends to the upper extremity of the limiter 80, and pivoted at their outer ends to the upper extremities of the links 74. In similar fashion, a pair of lower links 84 are pivoted at their outer ends to the lower extremities of the pair of links 74. The inner ends of the lower links 84 are pivotally secured by a ball joint connection 86, as best seen in FIGS. 10 and 12, to an upper strap 88. The strap 88 is connected by a pin 90 to a lower strap 92 for pivotal movement about an axis 94. The lower strap 92 is connected by a pin 96 to a mounting tab 98 for pivotal movement about an axis 100, as best seen in FIG. 12. The tab 98 is fixed to the keratometer housing 12.

In operation of the arrangement just described, the objective lens of the microscope is focused. Next, the keratometer 10 is moved toward or away from the cornea 18, as desired. This can be facilitated by attaching a removable, sterilizable handle or the like (not shown) to the keratometer housing 12. As will be apparent, the scissors mechanisms 73 are extensible to locate the keratometer 10 closer to the cornea 18, the amount of extension being adjustable by the surgeon. The lowermost position of the keratometer 10 relative to the lens barrel 56 is established by engagement between the pin 76 and the lowermost extremity of the slot 78.

The keratometer 10 can also be moved laterally to a limited extent by reason of the capability of the components for relative movement about the axes 94 and 100 and at the ball joints 86.

As an adjunct to quantitative keratometry the keratometer 10 may also be utilized with a reference device or test bar 102, as best seen in FIGS. 13 and 14.

The test bar 102 preferably takes the form of an elongated, generally rectangular plate made of sterilizable material and including a series of integrally formed convex test objects 104. The objects 104 are preferably black and characterized by shiny or reflective surfaces. Typically, the chord length of the convex surface is approximately 11.5 millimeters, which approximates the average chord lengths of a human cornea 18.

Each test object 104 is configured to represent a specific amount of corneal astigmatism. The first test object 104, located to the left in FIG. 13, has a perfectly spherical contour or configuration and represents zero astigmatism, expressed in diopters. The test objects to the right of this zero astigmatism object 104 have increasingly eliptical contours to represent increasing amounts of astigmatism. That is, as compared with the first test object, which has equal horizontal and vertical radii of curvature, the test objects to the right have an increasing difference between the horizontal and vertical radii of curvature to represent increasing astigmatism. The test bar 102 can be provided with various such test objects representing various corneal defects.

The test bar 102 can be used in lieu of the human cornea 18 to reflect light from the keratometer 10 and thereby aid in training surgeons in the use of the keratometer 10. In addition, during normal use of the keratometer 10 the test bar 102 is useful in quantitating the amount of astigmatism of the cornea 18 being observed. The appearance of a reflected image from the cornea is compared with the image reflected from the various test objects 104 until the comparison establishes the amount of astigmatism present.

Figure 5:
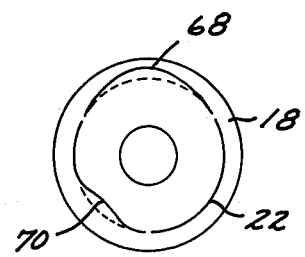
FIG. 5 is an elevational view of the cornea, illustrating the distortion of the reflected image from the periphery of the cornea which results when the radius of curvature is not normal.
Figure 6:
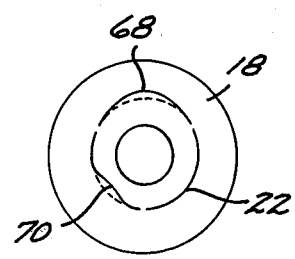
FIG. 6 is a view similar to FIG. 5, but illustrating the image reflected from a more central portion of the cornea upon location of the keratometer farther from the cornea.
Figure 7:
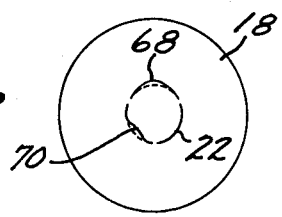
FIG. 7 is a view similar to FIG. 5, but illustrating the image reflected from the central portion of the cornea upon location of the keratometer still farther from the cornea.

According to the method of the present invention, the substantially continuous circle of light projected onto the cornea 18 permits relatively easy detection of meridional errors. If the radius of curvature of all meridia of the portion of the cornea 18 being examined are equal, a perfectly round or circular image 22 will be seen by the surgeon. If the radius of curvature of any meridian of that portion of the cornea is longer or shorter than the others, an oval distortion of the projected circle is seen. Thus, the image 22 is elongated, as seen at 68 in FIG. 5, when the radius of curvature is longer and the cornea 18 flatter than normal. Conversely, the image 22 is compressed, as seen at 70 in FIG. 5, when the radius of curvature is shorter and the cornea 18 steeper than normal. FIGS. 6 and 7 illustrate the same corneal distortion present as the keratometer 10 is moved farther from the cornea 18, reducing the size of the projected ring of light and thereby effecting reflection off the more central portions of the cornea 18.

Surgical procedures are known for manipulating the cornea 18 to effect compression of one meridian with a simultaneous elongation of the meridian perpendicular to the first. Thus, the relative curvature of the cornea 18 can be dynamically observed during surgery through use of the keratometer 10, and the cornea 18 then manipulated to produce an observed image 22 corresponding to the corneal curvature desired.

The keratometer 10 can be utilized to observe preoperative, operative and post-operative curvature of the cornea and is particularly useful in detecting the existence of meridional errors throughout the complete length of meridians extending between the cornea center and the corneal periphery.

As previously indicated, the keratometer can be disconnected from any structural support, in which case it can be hand held for use as a keratoscope.

Although the keratometer 10 has been described in connection with apparatus for projecting a circumferentially continous or substantially circumferentially continous circle of light, it is within the scope of the present invention to provide a plurality of concentric appertures 34 to effect reflection from the cornea of a plurality of concentric circles of light, which is useful in certain diagnostic and surgical procedures. Moreover, it is anticipated that other sources of light may be utilized in conjunction with the present keratometer 10. Thus, for example, high speed intermittent or stroboscopic flashes of light may be utilized as a light source for high intensity, low heat level light projection.

The term "keratometer" used in the following claims is intended to be interpreted broadly enough to comprehend use of the apparatus as a keratoscope.

Various modifications and changes may be made with regard to the foregoing detailed description without departing from the spirit of the invention.

We claim:
1. A keratometer comprising:
   a housing including means for projecting a single substantially circumferentially continuous circle of light onto a cornea for reflection of a generally circular image from the cornea, said housing further including walls defining a central opening free of any light refracting means having the effect of focusing said image, said image being observable along an axis extending through said opening; and
   support means for said housing, said support means being operable to systematically vary the distance between said housing and the cornea thereby to vary the diameter of said image without significant effect upon the sharpness of said image whereby said image may be progressively reflected from all portions of said cornea from the center of the cornea to the corneal periphery.
2. A keratometer according to claim 1 wherein said means in said housing includes a light source and an optical mask overlying said light source, said optical mask having a substantially continuous circumferential aperture for defining said circle of light.
3. A keratometer according to claim 2 wherein said optical mask includes a plurality of arcuate, individually continuous openings located upon a common circumference and relatively slightly spaced apart to define said substantially continuous circumferential aperture, the spaces between said openings being insufficient to significantly affect detection of a non-circular reflection of said circle of light.
4. A keratometer according to claim 2 wherein said light source comprises a tubular, circularly configured lamp operative to project said circle of light at a relatively low level of heat and at a relatively high level of light intensity whereby dynamic keratometry may be performed with full operating room illumination.
5. A keratometer according to claim 1 wherein said central opening is unobstructed whereby said image is observable by means of the unaided, naked eye, by means of magnifying loupes worn over the eyes, through an operating microscope, or via cameras.

6. A keratometer according to claim 1 wherein said support means is operable to vary said distance through an excursion of at least 300 to 400 millimeters.

7. A keratometer according to claim 1 wherein said housing includes clamping means for securing an optical instrument within said central opening for movement along said axis relative to said walls defining said opening.

8. A keratometer according to claim 7 wherein said optical instrument is a surgical microscope.

9. A keratometer according to claim 7 wherein said optical instrument is a camera.

10. A keratometer according to claim 1 wherein said support means comprises attachment means adapted for securement to a surgical microscope; longitudinally extensible and retractable means secured to said attachment means and to said housing and operative to enable extension and retraction of said housing independently of said surgical microscope.

11. A keratometer according to claim 10 wherein said support means include means enabling lateral movement of said housing relative to said attachment means.

12. A keratometer comprising:
a housing having a central opening and including means for projecting a single substantially circumferentially continuous circle of light onto a cornea for reflection from the cornea, said reflection being observable along an axis extending through said opening; and
support means for said housing, said support means comprising attachment means adapted for securement to a surgical microscope;
a pair of scissors mechanisms located on opposite sides of said attachment means and secured to said attachment means and to said housing and operative to enable extension and retraction of said housing relative to said surgical microscope and the cornea whereby warying the diameter of said circle is achieved without significant effect upon the sharpness thereof.

13. A method for performing keratometry and keratoscopy comprising the steps of:
projecting a substantially continuous circle of light onto a cornea from a centrally apertured housing and allowing the reflected image to pass unrefracted along an axis extending through the housing aperture; observing the unrefracted image; and
moving said housing progressively toward and away from the cornea whereby the diameter of said circle of light progressively enlarges and diminishes without significantly affecting the sharpness of said image whereby said circle of light traverses the cornea between the corneal periphery and the cornea center, respectively, thereby to detect in the unrefracted image meridional errors throughout the angular length of the meridians located between the cornea center and the corneal periphery.

14. A method according to claim 13 and including the step of projecting said circle of light onto a test object for comparison of the reflected image from said test object with the reflected image from said cornea.

15. Apparatus for performing keratometry and keratoscopy comprising:
a housing including a light source for projecting a substantially circumferentially continuous single circle of light onto a cornea for reflection of a generally circular image from the cornea, said housing further including walls defining a central opening free of any light refracting means having the effect of focusing said image, said image being observable along an axis extending through said opening, said housing being adapted to be hand held whereby the user can systematically vary the distance between said housing and the cornea thereby to vary the diameter of said image without significant effect upon the sharpness of said image whereby said image may be progressively reflected from all portions of said cornea from the center of the cornea to the corneal periphery.

* * * * *